(12) United States Patent
Shibata et al.

(10) Patent No.: US 7,759,709 B2
(45) Date of Patent: Jul. 20, 2010

(54) SOLID-STATE IMAGING DEVICE AND IMAGING APPARATUS

(75) Inventors: Ikuya Shibata, Osaka (JP); Wataru Kamisaka, Shiga (JP); Kozo Orihara, Kyoto (JP)

(73) Assignee: Panasonic Corporation, Osaka (JP)

( * ) Notice: Subject to any disclaimer, the term of this patent is extended or adjusted under 35 U.S.C. 154(b) by 6 days.

(21) Appl. No.: 12/204,317

(22) Filed: Sep. 4, 2008

(65) Prior Publication Data
US 2009/0189197 A1   Jul. 30, 2009

(30) Foreign Application Priority Data
Jan. 29, 2008   (JP) .............................. 2008-017110

(51) Int. Cl.
*H01L 27/00* (2006.01)
(52) U.S. Cl. ................................. 257/233; 257/E27.15
(58) Field of Classification Search ................. 257/233, 257/E27.15
See application file for complete search history.

(56) References Cited
U.S. PATENT DOCUMENTS
5,796,171 A   8/1998   Koc et al.
5,818,114 A   10/1998   Pendse et al.
5,892,276 A   4/1999   Miki et al.
2005/0253044 A1 * 11/2005   Kuriyama ................ 250/208.1
2006/0011813 A1   1/2006   Park et al.

FOREIGN PATENT DOCUMENTS
JP   63-303580   12/1988
JP   2002-329742   11/2002

* cited by examiner

*Primary Examiner*—Thanh V Pham
*Assistant Examiner*—Marvin Payen
(74) *Attorney, Agent, or Firm*—McDermitt Will & Emery LLP

(57) ABSTRACT

A solid-state imaging device includes: an imaging region including a plurality of light-receiving parts; a first transfer section provided on the imaging region and transferring, in a first direction, signals generated by the light-receiving parts; a second transfer section provided at a first side of the imaging region and transferring, in a second direction intersecting the first direction, the signals transferred from the first transfer section; an output circuit for outputting the signals; and bonding pads provided at the first side of the imaging region with the second transfer section sandwiched between the imaging region and the bonding pads. The bonding pads are arranged in a plurality of rows each extending in the second direction. Each of the bonding pads in one of the rows at least partially overlaps one of the bonding pads in another one of the rows when viewed in the first direction.

9 Claims, 9 Drawing Sheets

SOLID-STATE IMAGING DEVICE AND IMAGING APPARATUS

BACKGROUND OF THE INVENTION (1) Field of the Invention

The present invention relates to solid-state imaging devices and imaging apparatus including the same, and particularly relates to arrangements of bonding pads in solid-state imaging devices.

(2) Disclosure of Related Art

In recent years, endoscopes equipped with solid-state imaging devices which are in the form of chips and include light-receiving parts are widely used for industrial, medical, and other purposes. Industrial endoscopes are useful for, for example, observing and inspecting the inside of machinery, piping, or other objects. Medical endoscopes are very useful for, for example, minimally invasive surgery and gastrointestinal examinations.

Japanese Laid-Open Patent Publication No. 63-303580 discloses an endoscope including a solid-state imaging device. FIGS. 9A and 9B are a side view and a plan view, respectively, schematically illustrating a structure of a conventional endoscope. FIG. 10 is a plan view illustrating a solid-state imaging device in the endoscope disclosed in Japanese Laid-Open Patent Publication No. 63-303580. FIGS. 9A and 9B show an internal structure when viewed through a filler 158.

As illustrated in FIGS. 9A and 9B, the conventional endoscope includes: a lens (camera lens) 151; a prism 152 for bending, to a right angle, the optical axis of incident light 159 which has passed through the lens 151; a solid-state imaging device 153 including an imaging region 154 and bonding pads 155; a board 156 having an upper face on which the solid-state imaging device 153 is fixed; wires 157 whose one ends are bonded to the bonding pads 155 and another ends are connected to, for example, a board (not shown) outside the solid-state imaging device 153; and the filler 158 encapsulating the prism 152 and the solid-state imaging device 153. The shape of this endoscope is tubular.

As illustrated in FIG. 10, a conventional solid-state imaging device 161 includes: an imaging region 154; vertical charge coupled devices (CCDs) 163 provided on the imaging region 154 and used for transferring signal charge read out from photodiodes 162 in the vertical direction (i.e., the left-right direction in FIG. 10); horizontal CCDs 164 placed at a side of the imaging region 154 and used for transferring the signal charge from the vertical CCDs 163 in the horizontal direction (i.e., the up-down direction in FIG. 10); an output circuit 165 for outputting the signal charge from the horizontal CCDs 164; and a plurality of bonding pads 168 provided in a region vertically located to the imaging region 154 and the horizontal CCDs 164 (i.e., a region located at the right side of the imaging region 154 and the horizontal CCDs 164 in the FIG. 10).

The photo diodes 162 are arranged in rows and columns in the imaging region 154. The bonding pads 168 are aligned with a given spacing in the horizontal direction along a side of the solid-state imaging device. The bonding pads 168 receive signals for driving the vertical CCDs and the horizontal CCDs and signals to be supplied to the output circuit 165. Signals from the output circuit 165 are transmitted to the outside of the solid-state imaging device via the bonding pads 168.

The solid-state imaging device 153 is incorporated in the tip of an insertion portion of the endoscope as described above. In particular, medical endoscopes are required to have smaller outside diameters of their insertion portions in order to relieve pain of patients. For this purpose, the insertion portion of the conventional endoscope is provided with the prism 152 for bending the optical axis of incident light 159 to a right angle and is also provided with the solid-state imaging device 153 disposed in such a manner that the direction from the imaging region 154 to the bonding pads 155 coincides with the axis of the endoscope. This structure allows reduction of the outside diameter of the insertion portion.

However, many patients still feel discomfort with gastroscopes and colonoscopies, so that endoscopes with much smaller outside diameters are demanded. In addition, reduction in outside diameter of endoscopes in endoscopic surgery further lessens a burden on patients.

Recent development of integrated circuit technology has greatly reduced the size of imaging regions of solid-state imaging devices. On the other hand, great reduction in size of bonding pads is still difficult because it is necessary to maintain a certain connection strength and an area to be in contact with a probe during inspection. It is also necessary to dispose adjacent bonding pads with a given spacing for, for example, manufacturing reasons, thus making it difficult to reduce the distance between the bonding pads in order to reduce the horizontal width of a solid-state imaging device.

SUMMARY OF THE INVENTION

It is therefore an object of the present invention to provide a solid-state imaging device with which imaging apparatus such as an endoscope with a small outside diameter is implemented.

A solid-state imaging device according to the present invention includes: an imaging region including a plurality of light-receiving parts for converting incident light into signals; a first transfer section provided on the imaging region and transferring, in a first direction, the signals generated by the light-receiving parts; a second transfer section provided at a first side of the imaging region in the first direction and transferring, in a second direction intersecting the first direction, the signals transferred from the first transfer section; an output circuit for outputting the signals transferred from the second transfer section; and a plurality of bonding pads provided at the first side of the imaging region with the second transfer section sandwiched between the imaging region and the bonding pads, wherein the bonding pads are arranged in a plurality of rows each extending in the second direction, and each of the bonding pads in one of the rows at least partially overlaps one of the bonding pads in another one of the rows when viewed in the first direction.

In a conventional solid-state imaging device, the width of a region necessary for bonding pads is larger than the width of the imaging region in the second direction, so that it is difficult to reduce the width in the second direction. On the other hand, in the solid-state imaging device of the present invention, the bonding pads are arranged in a plurality of rows and the bonding pads in different rows at least partially overlap each other when viewed in the first direction. Accordingly, the width of a region necessary for arranging the bonding pads is greatly reduced. Thus, the application of the inventive solid-state imaging device to imaging apparatus whose length in the longitudinal direction is larger than the lateral direction thereof enables reduction in outside diameter of the imaging apparatus.

In the solid-state imaging device of the present invention, since the bonding pads are arranged in a plurality of rows, the width in the first direction is larger than conventional devices. Accordingly, the solid-state imaging device of the present invention is preferably applied to imaging device required to have its width in one direction reduced, such as endoscopes, rather than imaging device whose longitudinal length and lateral length both need to be reduced, such as typical digital cameras.

An imaging apparatus according to the present invention includes: a first optical member for focusing light; a second optical member for bending an optical axis of the light that has passed through the first optical member and for emitting the resultant light; a solid-state imaging device including an imaging region including a plurality of light-receiving parts for converting the light from the second optical member into signals, a first transfer section provided on the imaging region and transferring, in a first direction, the signals generated by the light-receiving parts, a second transfer section provided at a first side of the imaging region in the first direction and transferring, in a second direction intersecting the first direction, the signals transferred from the first transfer section, an output circuit for outputting the signals transferred from the second transfer section, and a plurality of bonding pads provided at the first side of the imaging region with the second transfer section sandwiched between the imaging region and the bonding pads; an electronic board connected to the bonding pads; and connecting members for connecting the bonding pads to the electronic board, wherein the bonding pads are arranged in a plurality of rows each extending in the second direction, each of the bonding pads in one of the rows at least partially overlaps one of the bonding pads in another one of the rows when viewed in the first direction, and the first direction coincides with the optical direction of the light incident on the second optical member.

With this structure, the bonding pads at a side of the imaging region are arranged in a plurality of rows, thereby reducing the width of the solid-state imaging device in the second direction, as compared to conventional devices. In addition, the solid-state imaging device is placed such that the first direction coincides with the optical axis of light incident on the second optical member, thereby greatly reducing the outside diameter of imaging apparatus, as compared to conventional apparatus.

As described above, in the solid-state imaging device of the present invention, bonding pads are arranged in a plurality of rows at a side of an imaging region in a first direction and bonding pads in different rows at least partially overlap one another when viewed in the first direction, so that the width of the solid-state imaging device in the first direction is greatly reduced. Accordingly, the outside diameter of imaging apparatus provided in the inventive solid-state imaging device in the second direction is much smaller than those of conventional apparatus.

DETAILED DESCRIPTION OF THE INVENTION

Hereinafter, preferred embodiments of the present invention will be specifically described with reference to the accompanying drawings.

Embodiment 1

Figure 1:
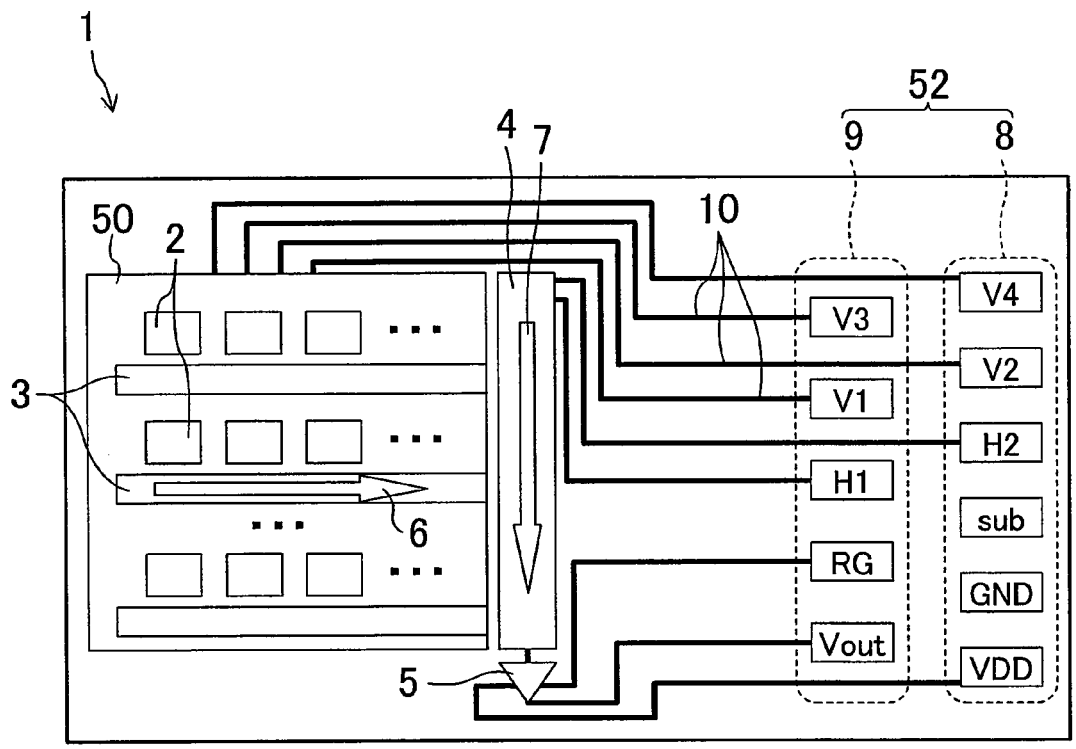
FIG. 1 is a plan view illustrating a solid-state imaging device according to a first embodiment of the present invention.

FIG. 1 is a plan view illustrating a solid-state imaging device according to a first embodiment of the present invention. The "solid-state imaging device" herein refers to a structure formed on one semiconductor substrate.

As shown in FIG. 1, a solid-state imaging device 1 of this embodiment includes: an imaging region 50 in which light-receiving parts, such as photodiodes 2, for converting light into signal charge are arranged in two dimensions; vertical CCDs (a first transfer section) 3 for transferring the signal charge from the photodiodes 2 in the vertical direction (i.e., the left-right direction in FIG. 1: first direction); horizontal CCDs (a second transfer section) 4 placed at a side of the imaging region 50 and used for transferring the signal charge from the vertical CCDs 3 in the horizontal direction (i.e., the up-down direction in FIG. 1: second direction); an output circuit 5 for outputting the signal charge from the horizontal CCDs 4; and a plurality of bonding pads 52 provided at the side of the imaging region 50 in the vertical direction (i.e., at the right side in FIG. 1) with the horizontal CCDs 4 sandwiched therebetween; and lines 10 each extending from one of the bonding pads 52 to one of the imaging region 50, the horizontal CCDs 4 or the output circuit 5. In FIG. 1, reference numeral 6 denotes a transfer direction of signal charge in the vertical CCDs 3, and reference numeral 7 denotes a transfer direction of signal charge in the horizontal CCDs 4.

The solid-state imaging device 1 of this embodiment is characterized in that the bonding pads 52 are arranged in a plurality of rows each extending in the second direction (i.e., the transfer direction 7 in the horizontal CCDs 4) and each of the bonding pads 52 at least partially overlaps one of the bonding pads 52 in a different row when viewed in the first direction. In the example shown in FIG. 1, the bonding pads 52 are divided into two rows: a first bonding pad row 8; and a second bonding pad row 9 which is closer to the imaging region 50 than the first bonding pad row 8. In other words, the bonding pads 52 are staggered at the side of the imaging region 50 in the first direction. The first bonding pad row 8 and the second bonding pad row 9 do not overlap each other when viewed in the second direction.

This arrangement greatly reduces the width of the solid-state imaging device 1 in the second direction (i.e., the signal transfer direction in the horizontal CCDs 4), as compared to conventional arrangements. The distance between the bonding pads in the first bonding pad row 8 and the distance between the bonding pads in the second bonding pad row 9 are equal to that in the case of arranging the bonding pads in one row. Accordingly, in the arrangement in which the bonding pads 52 are divided into two rows as in this embodiment, the width in the second direction of the region where the bonding pads 52 are provided is reduced to ½ at a minimum. Therefore, when the solid-state imaging device of this embodiment is applied to imaging apparatus such as an endoscope, inspection apparatus, or a camera, the outside diameter, especially the outside diameter of an insertion portion, of the imaging apparatus is allowed to be greatly reduced.

The arrangement of the bonding pads 52 in a plurality of rows increases the width in the first direction. However, in the application of the solid-state imaging device of this embodiment to slender imaging apparatus such as endoscopes, the increase in width in the first direction causes no problems as long as the first direction coincides with the longitudinal direction of the imaging apparatus.

In FIG. 1, reference numeral Vout denotes an output pad for outputting a signal output from the output circuit 5 to the outside, reference numeral VDD denotes a power-supply pad for supplying a power supply voltage to the output circuit 5, reference numeral GND denotes a ground pad, and reference numeral sub denotes a substrate contact pad. Reference numeral RG denotes a reset pad for supplying a reset drive pulse to the output circuit 5, reference numerals H1 and H2 denote drive pads for supplying drive pulses to the horizontal CCDs 4, and reference numerals V1 through V4 denote drive pads for supplying drive pulses to the vertical CCDs 3. The arrangement of the pads is not limited to this, and may be in any form as long as the lines 10 do not intersect. The pads Vout, VDD, GND and sub are direct-current terminals, whereas the pads RG, H1, H2 and V1 through V4 are alternating-current terminals.

The shape of each of the bonding pads 52 is not specifically limited, but, as shown in FIG. 1, a rectangle whose length in the first direction is larger than that in the second length is especially preferable. After fabrication, the solid-state imaging device is inspected with a tester before being connected to an external board or other components. In this inspection, a probe comes into contact with the bonding pads 52. The surface in contact with the probe becomes rough, so that formation of connecting members such as bumps and wires on this surface causes drawbacks such as decrease in connection strength. A portion where each of the bonding pads 52 is in contact with a bump or a wire is approximately circular in plan view. Therefore, when the bonding pads 52 are rectangular, the bonding pads 52 inevitably have portions, e.g., at the corners thereof, which are not used for connection to connecting members. In view of this, these portions are used as inspection pads to be in contact with the probe, thereby avoiding connection failures. The portions to be in contact with the probe are not limited to the corners but may be the left half of each of the bonding pads 52 so that the right half thereof is used for connection to a connecting member.

When the solid-state imaging device is quadrilateral in plan view, the bonding pads 52 are preferably provided at a side of the imaging region 50 in the first direction, and are more preferably located at the side of the imaging region 50 with the horizontal CCDs 4 sandwiched between the imaging region 50 and the bonding pads 52. When the bonding pads 52 are provided at the side of the imaging region 50 in the first direction, orientation of the solid-state imaging device in which the first direction coincides with the optical axis (i.e., the longitudinal axis of imaging apparatus) of light incident on the prism of the imaging apparatus allows a defect-free image to be obtained. Further, when the bonding pads 52 are located such that the horizontal CCDs 4 are sandwiched between the imaging region 50 and the bonding pads 52, the length of the lines 10 connected to the output circuit 5 or the horizontal CCDs 4 is reduced, thus easing formation of wiring pattern.

As is clear when the pads H1, VDD, and V4, for example, are compared with one another, the connection portions between some of the bonding pads 52 and associated ones of the lines 10 shift in the second direction as necessary depending on the locations of the bonding pads 52 in the solid-state imaging device of this embodiment. This minimizes the wiring layout of the lines 10, while maintaining sufficient distances between the bonding pads 52 and between the lines 10.

In FIG. 1, six pads form the first bonding pad row 8 and five pads form the second bonding pad row 9. Alternatively, as in a solid-state imaging device according to a modified example of the first embodiment shown in FIG. 2, the number of pads in an inner second bonding pad row 12 may be larger than that of pads in an outer first bonding pad row 11. That is, the number of bonding pads forming each row is not specifically limited. However, lines 10 connected to the bonding pads in the first bonding pad row are located between adjacent bonding pads in the second bonding pad row. Thus, the number of pads in the first bonding pad row is preferably equal to or larger than that in the second bonding pad row in order to increase flexibility in pad arrangement. However, in some cases, the number of pads in the second bonding pad row is preferably larger than the number of pads in the first bonding pad row depending on design, e.g., in the case where a peripheral circuit is provided adjacent to the first bonding pad row.

Figure 2:
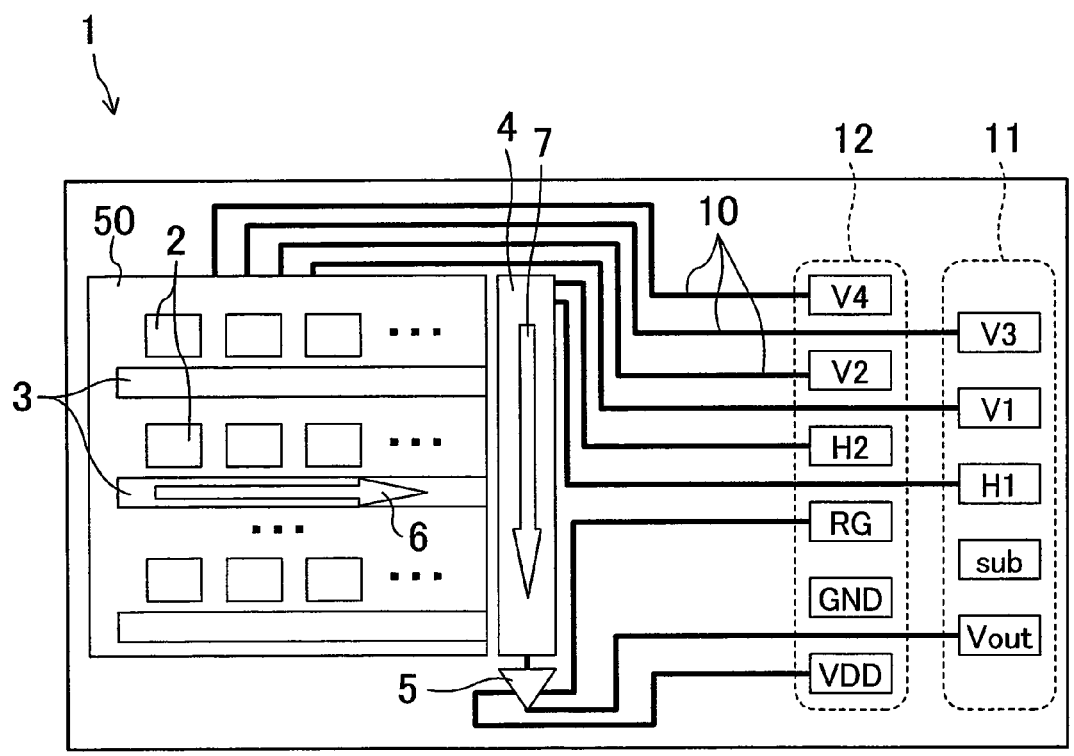
FIG. 2 is a plan view illustrating a solid-state imaging device according to a modified example of the first embodiment.

In addition, as shown in FIG. 2, the output pad Vout may be adjacent to the direct-current terminals and separated from the alternating-current terminals. This arrangement suppresses occurrence of cross-talk, thus preventing degradation of image quality.

The solid-state imaging device 1 of this embodiment is applicable not only to a tubular endoscope but also to a slender capsule endoscope. The solid-state imaging device 1 is also preferably used for endoscopes for any purpose such as medical or industrial purpose.

The bonding pads 52 only need to be arranged in a plurality of rows. For example, the bonding pads 52 may be arranged such that the bonding pads in the first bonding pad row 8 and the bonding pads in the second bonding pad row 9 completely overlap one another when viewed in the first direction. However, when wires are used as connecting members for connection to an external board, an arrangement in which bonding pads 52 respectively belonging to different rows partially overlap one another when viewed in the first direction is preferable in order to prevent contact between wires.

Embodiment 2

Figure 3:
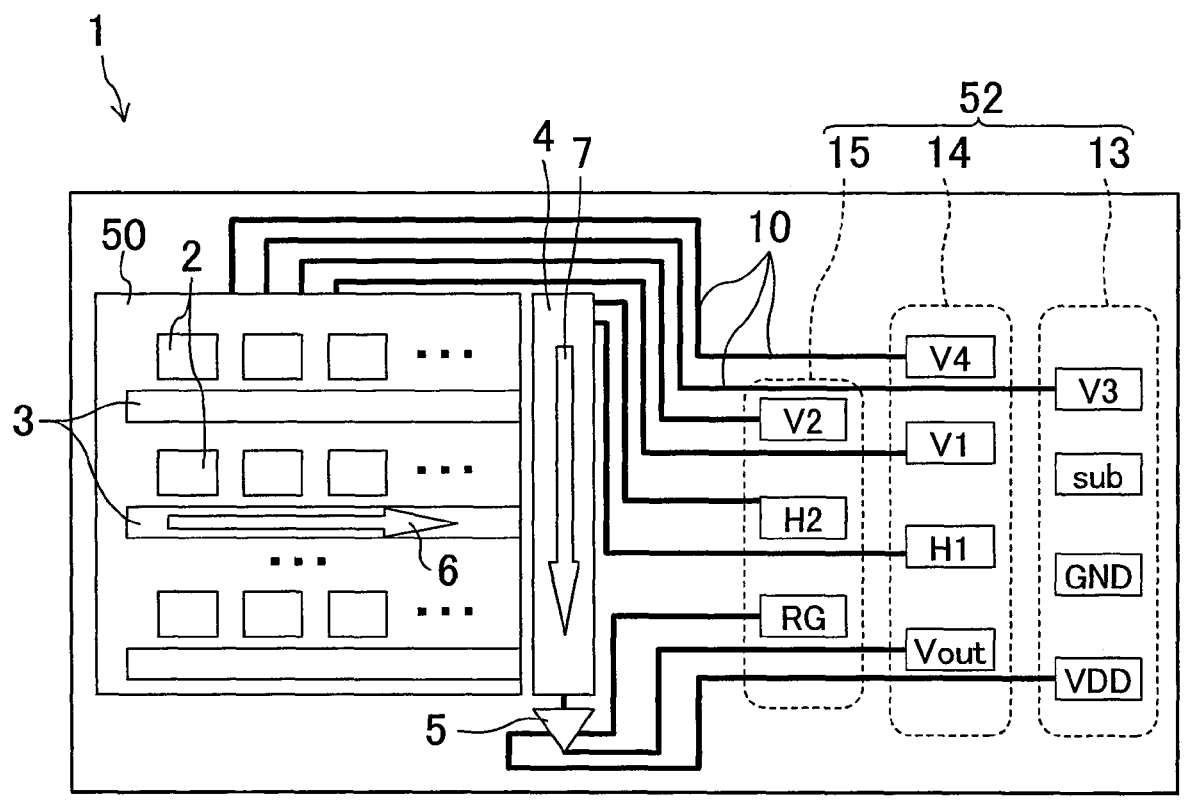
FIG. 3 is a plan view illustrating a solid-state imaging device according to a second embodiment of the present invention.

FIG. 3 is a plan view illustrating a solid-state imaging device according to a second embodiment of the present invention. In FIG. 3, components already shown in FIG. 1 are denoted by the same reference numerals, and description thereof will be omitted.

As in the solid-state imaging device of the first embodiment, in the solid-state imaging device of the second embodiment, bonding pads 52 are provided in a region at a side of an imaging region 50 in a first direction with horizontal CCDs 4 sandwiched between the imaging region 50 and the bonding pads 52. In this embodiment, the bonding pads 52 are arranged such that three rows of a third bonding pad row 15, a second bonding pad row 14, and a first bonding pad row 13 are located in this order from the imaging region 50. This arrangement of the bonding pads 52 further reduces the width of the solid-state imaging device 1 in a second direction. Accordingly, the use of the solid-state imaging device 1 of this embodiment further reduces the outside diameter of an endoscope, thus relieving pain of patients.

The bonding pads 52 are not necessarily arranged in three rows and may be arranged in four or more rows. In such a case, even with a large number of bonding pads 52, the width of the solid-state imaging device 1 in the second direction is greatly reduced as compared to conventional solid-state imaging devices.

Embodiment 3

Figure 4:
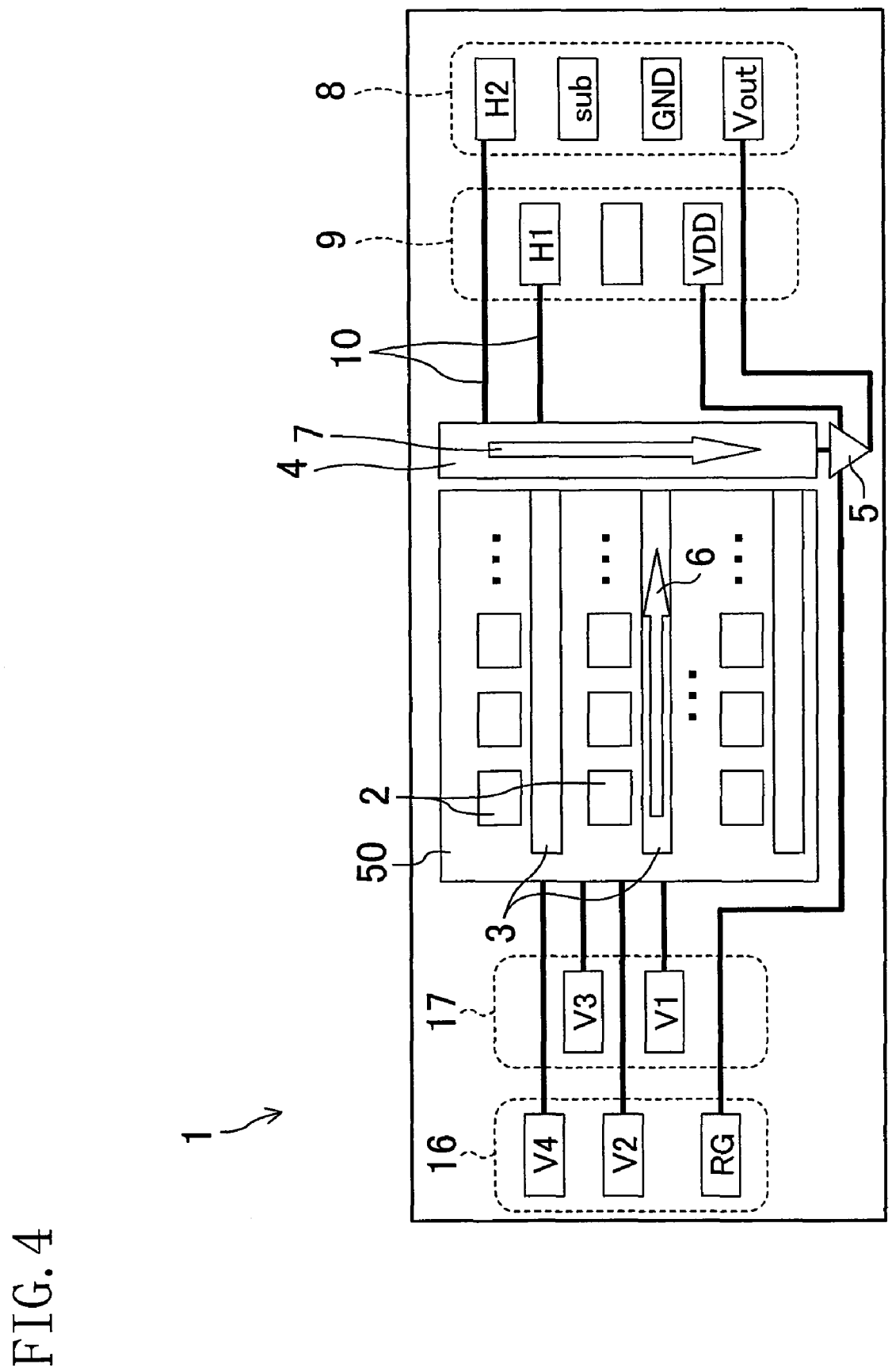
FIG. 4 is a plan view illustrating a solid-state imaging device according to a third embodiment of the present invention.

FIG. 4 is a plan view illustrating a solid-state imaging device according to a third embodiment of the present invention. In FIG. 4, components already shown in FIG. 1 are denoted by the same reference numerals, and description thereof will be omitted.

In the solid-state imaging device of this embodiment, bonding pads are provided at both sides of an imaging region 50 in a first direction. The bonding pads at each side are arranged in a plurality of (e.g., two in FIG. 4) rows.

This arrangement further reduces the width of the solid-state imaging device 1 in the second direction, as compared to the solid-state imaging device of the first embodiment.

In the solid-state imaging device 1 of this embodiment, pads V1 through V4 receiving alternating-current signals belong to fourth and fifth bonding pad rows 16 and 17 and are provided at the side of the imaging region 50 opposite an output pad Vout. With this arrangement, the pads V1 through V4 receiving high-frequency signals are separated from the output pad Vout, thereby effectively avoiding occurrence of cross-talk while preventing a wiring pattern from being complicated.

Embodiment 4

Figure 5:
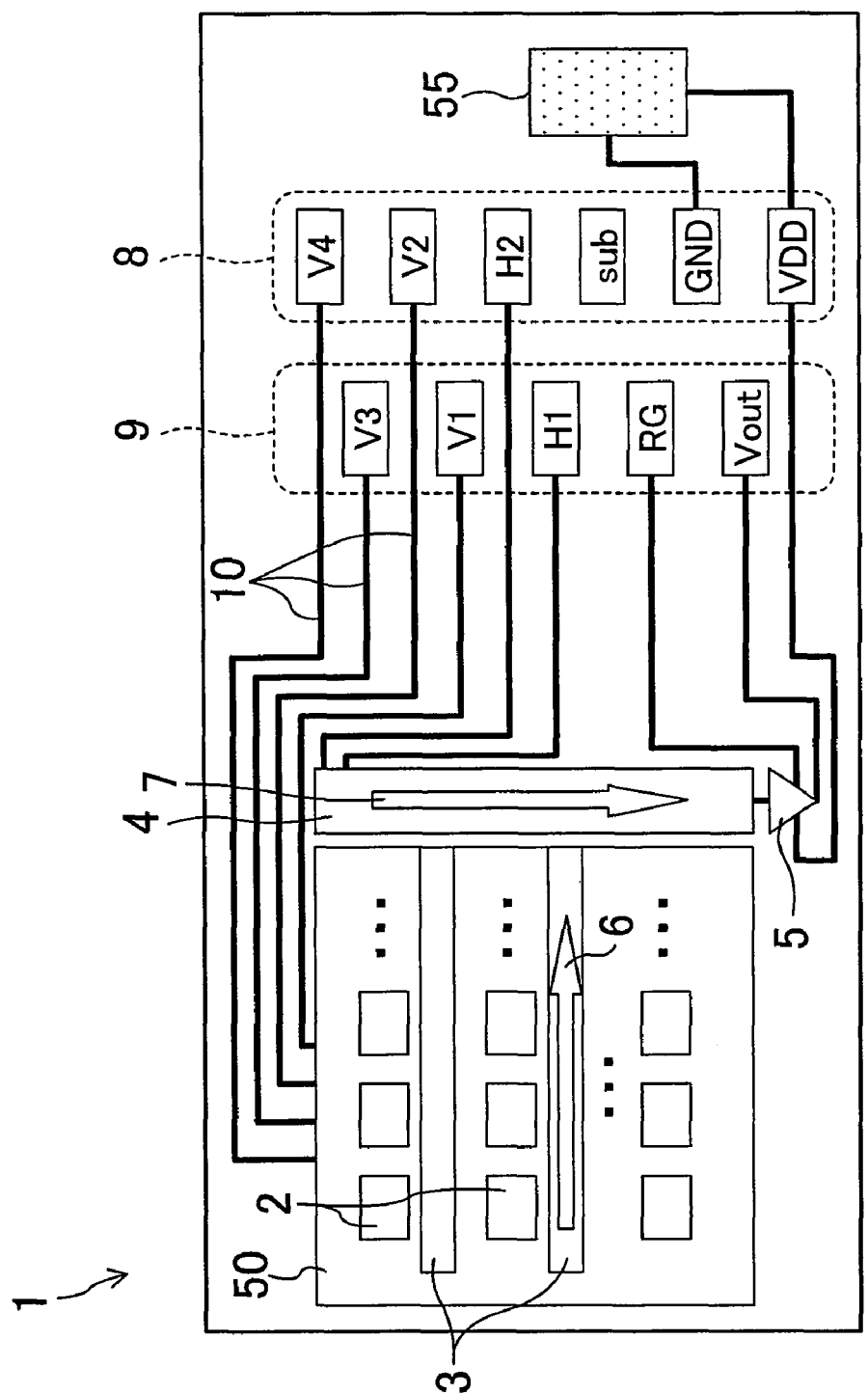
FIG. 5 is a plan view illustrating a solid-state imaging device according to a fourth embodiment of the present invention.

FIG. 5 is a plan view illustrating a solid-state imaging device according to a fourth embodiment of the present invention. In FIG. 5, components already shown in FIG. 1 are denoted by the same reference numerals, and description thereof will be omitted.

In the solid-state imaging device of this embodiment, bonding pads arranged in a plurality of rows are located between an internal-voltage generating circuit 55, serving as a peripheral circuit, and an imaging region 50. The internal-voltage generating circuit 55 is used for generating a substrate voltage and a direct-current voltage necessary for setting an operation point of an output circuit 5, and is formed of two or more resistors provided between, for example, a power-supply pad VDD and a ground pad GND.

The internal-voltage generating circuit 55 generates an arbitrary voltage by utilizing resistance division of the resistors made of, for example, polysilicon, thereby providing heat. Size reduction of the solid-state imaging device involves the necessity for size reduction of the resistors. With increase in resistance, heat generated at the internal-voltage generating circuit 55 increases.

In the solid-state imaging device of this embodiment, the internal-voltage generating circuit 55 as a heat source is located as far away from the imaging region 50 as possible, thereby greatly reducing noise caused by heat, as compared to conventional devices. Accordingly, the solid-state imaging device of this embodiment prevents degradation of image quality caused by noise.

In the foregoing example, the peripheral circuit generating heat is the internal-voltage generating circuit. However, the circuit to be located away from the imaging region 50 is not specifically limited as long as the circuit generates heat. Specifically, an impedance-matching output circuit may be provided closer to the outside than the first bonding pad row 8. This impedance-matching output circuit is a source follower circuit provided at a subsequent stage of the output circuit 5 and composed of a MOSFET and a resistor. In the case of incorporating a solid-state imaging device in an endoscope, the solid-state imaging device is driven via a cable with a length of about several meters. Thus, to take matching between cable load and impedance, a large current is caused to flow in the source follower circuit to suppress blunting of an output waveform. Thus, the impedance-matching output circuit that generates heat is kept away from the imaging region 50, resulting in effectively suppressing occurrence of noise.

Embodiment 5

Figure 6:
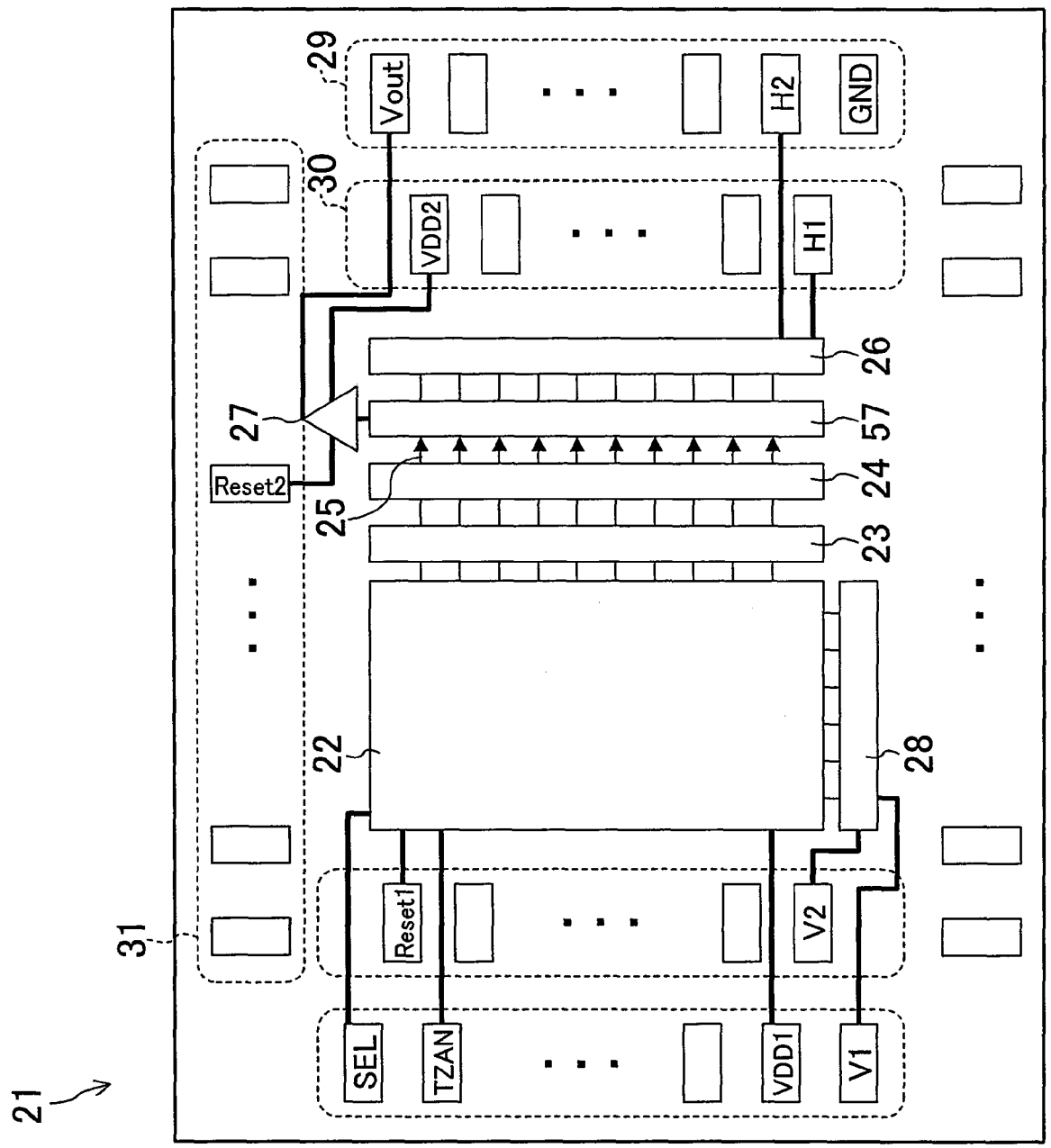
FIG. 6 is a plan view illustrating a solid-state imaging device according to a fifth embodiment of the present invention.

FIG. 6 is a plan view illustrating a solid-state imaging device according to a fifth embodiment of the present invention. In the solid-state imaging device of this embodiment, the arrangement of bonding pads described above is applied to a MOS solid-state imaging device.

As shown in FIG. 6, a solid-state imaging device 21 of this embodiment includes: an imaging region (pixel array) 22 in which light-receiving parts for converting light into signal charge are arranged in two dimensions; vertical signal lines (a first transfer section) for transferring signals read out from photodiodes 2 in the vertical direction (i.e., the left-right direction in FIG. 6: first direction); a vertical shift register 28 for causing signals generated by the light-receiving parts to be sequentially read out to the vertical signal lines; column amplifiers 23 provided for the respective vertical signal lines and used for amplifying signals output from the light-receiving parts; column correlated double sampling (CDS) circuits 24 receiving outputs from the column amplifiers 23; horizontal signal lines (a second transfer section) 57 for transferring signals subjected to processing of the column CDS circuits 24 in the horizontal direction (i.e., the up-down direction in FIG. 6: second direction) that intersects the first direction; selection circuits 25 provided between the horizontal signal lines 57 and the column CDS circuits 24; a horizontal shift register 26 for controlling the selection circuits 25 such that the signals in the respective columns are sequentially read out to the horizontal signal lines 57; an output amplifier (output circuit) 27 for outputting signals read out to the horizontal signal lines 57; and a plurality of bonding pads.

In the solid-state imaging device 21 of this embodiment, the bonding pads are provided in regions in four directions from the imaging region 22. In particular, a first bonding pad row 29 and a second bonding pad row 30 are provided in a region located at a side of the imaging region 22 in the first direction with the horizontal signal lines 57 and the horizontal shift register 26 sandwiched between the imaging region 22 and the first and second bonding pad rows 29 and 30. In the same manner, two rows of bonding pads are provided in a region located at the other side of the imaging region 22 in the first direction, i.e., at the side of the imaging region 22 opposite the horizontal signal lines 57. A MOS solid-state imaging device needs a larger number of pads for driving than a CCD solid-state imaging device, so that one bonding pad column (i.e., a single bonding pad column 31) is provided in a region located at a side of the imaging region 22 in the second direction in the solid-state imaging device 21 of this embodiment. In FIG. 6, reference numeral VDD1 denotes a power supply pad for a pixel array, reference numeral TZAN denotes a pad receiving a signal for reading a signal from the pixel array, reference numeral Reset1 denotes a reset pad for resetting a signal held in a pixel, reference numeral SEL denotes a selection-signal pad for selecting a pixel from which a signal is to be read out, reference numerals H1 and H2 denote drive pads for supplying drive pulses to the horizontal shift register 26, reference numerals V1 and V2 denote drive pads for supplying drive pulses to the vertical shift register 28; reference numeral VDD2 denotes a power-supply pad for supplying a power supply voltage for the output amplifier 27; reference numeral Reset2 denotes a reset pad for supplying a reset voltage to the output amplifier 27; reference numeral Vout denotes an output pad for outputting a signal from the output amplifier 27 to the outside; and reference numeral GND denotes a ground pad. The arrangement of the pads is not limited to that shown in FIG. 6. Specifically, the output pad Vout may be located adjacent to only the direct-current terminals so that the output pad Vout is separated from the alternating-current terminals so as to reduce cross-talk.

As in the solid-state imaging device of the first embodiment, in the solid-state imaging device 21 of the fifth embodiment, the first bonding pad row 29 and the second bonding pad row 30 are located at the side of the imaging region 22 in the first direction and partially overlap each other when viewed in the first direction, so that the width in the second direction is greatly reduced, as compared to conventional solid-state imaging devices. In this manner, the arrangement of pads according to the present invention is very effective in reducing the outside diameter of imaging apparatus even for a MOS solid-state imaging device. In particular, since a MOS solid-state imaging device needs a larger number of bonding pads than a CCD solid-state imaging device, bonding pads are arranged in a plurality of rows at a side of the imaging region 22, thereby drastically reducing the width in the second direction. This allows the MOS solid-state imaging device to be applicable to imaging apparatus with a small diameter, such as an endoscope.

Figure 7:
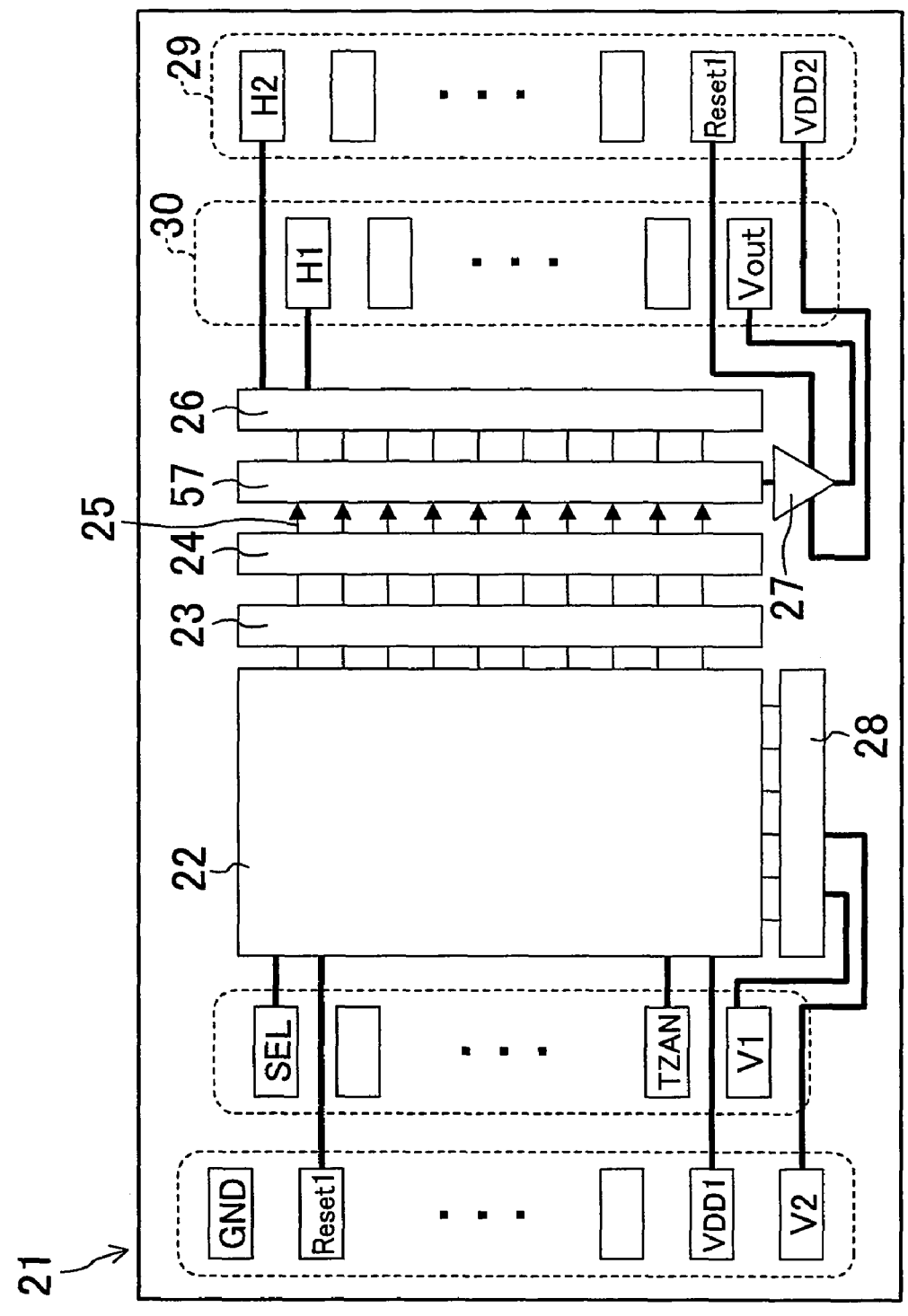
FIG. 7 is a plan view illustrating a solid-state imaging device according to a modified example of the fifth embodiment.

FIG. 7 is a plan view illustrating a solid-state imaging device according to a modified example of this embodiment. As shown in FIG. 7, bonding pads may be provided only at the sides of the imaging region 22 in the first direction so that the width of the solid-state imaging device in the second direction is reduced. This arrangement further reduces the width of the solid-state imaging device in the second direction, as compared to the solid-state imaging device shown in FIG. 6. The direction of signal transmission in the horizontal signal lines 57 may be any of a rightward direction (i.e., the direction shown in FIG. 7) and a leftward direction (i.e., the direction shown in FIG. 6) when viewed from the imaging region 22 as long as the signal is transmitted along the second direction (i.e., the up-down direction in FIG. 7).

Embodiment 6

Figure 8A:
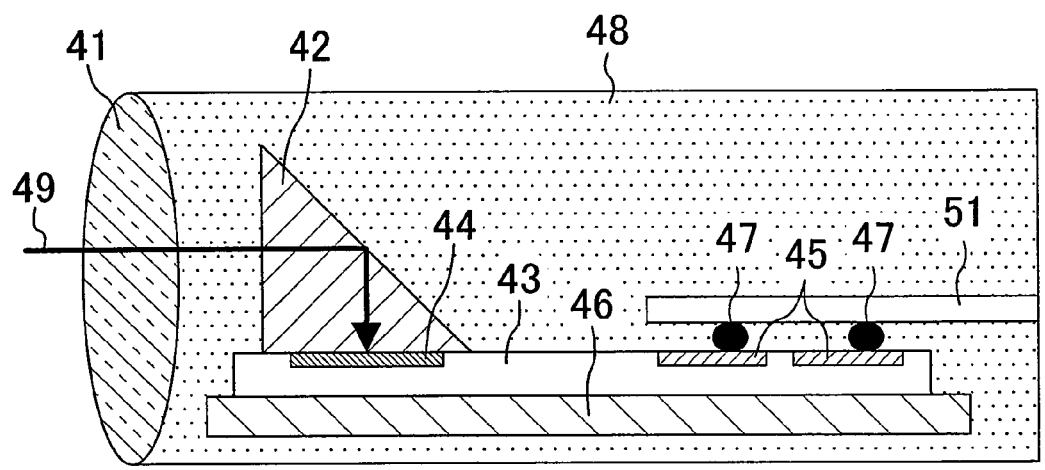
FIGS. 8A and 8B are a side view and a plan view, respectively, schematically illustrating imaging apparatus according to a sixth embodiment of the present invention.
Figure 8B:
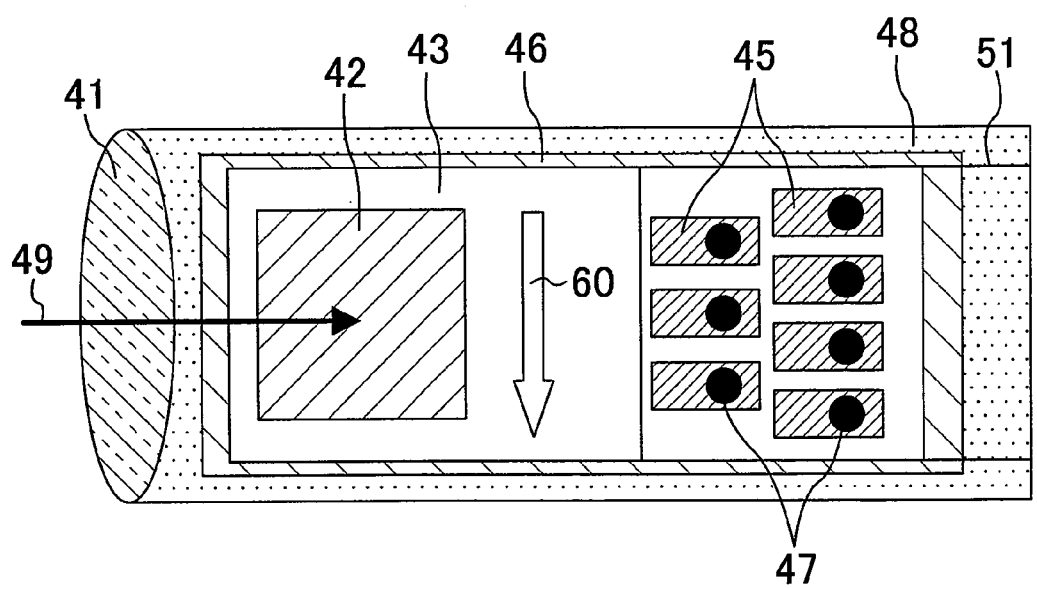
Figure 9A:
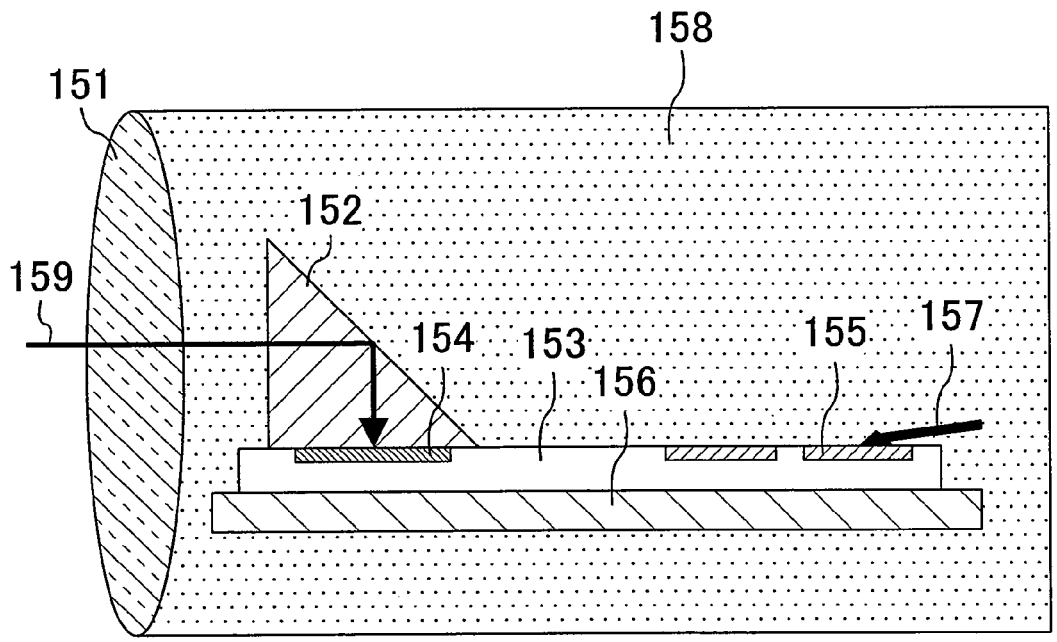
FIGS. 9A and 9B are a side view and a plan view, respectively, schematically illustrating a conventional endoscope.
Figure 9B:
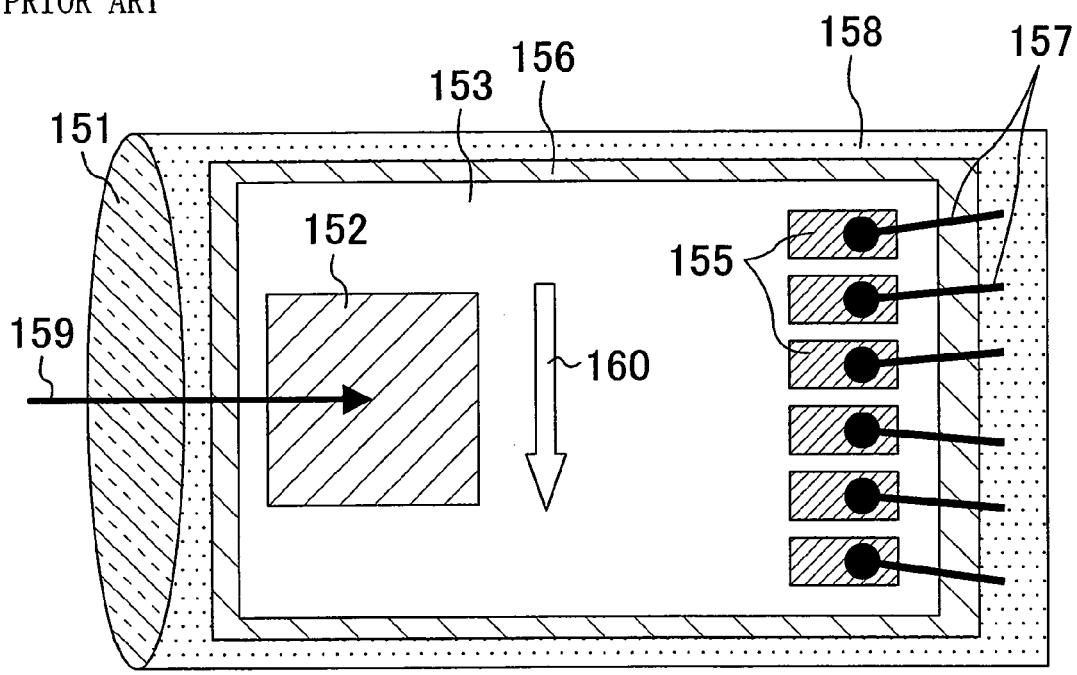
Figure 10:
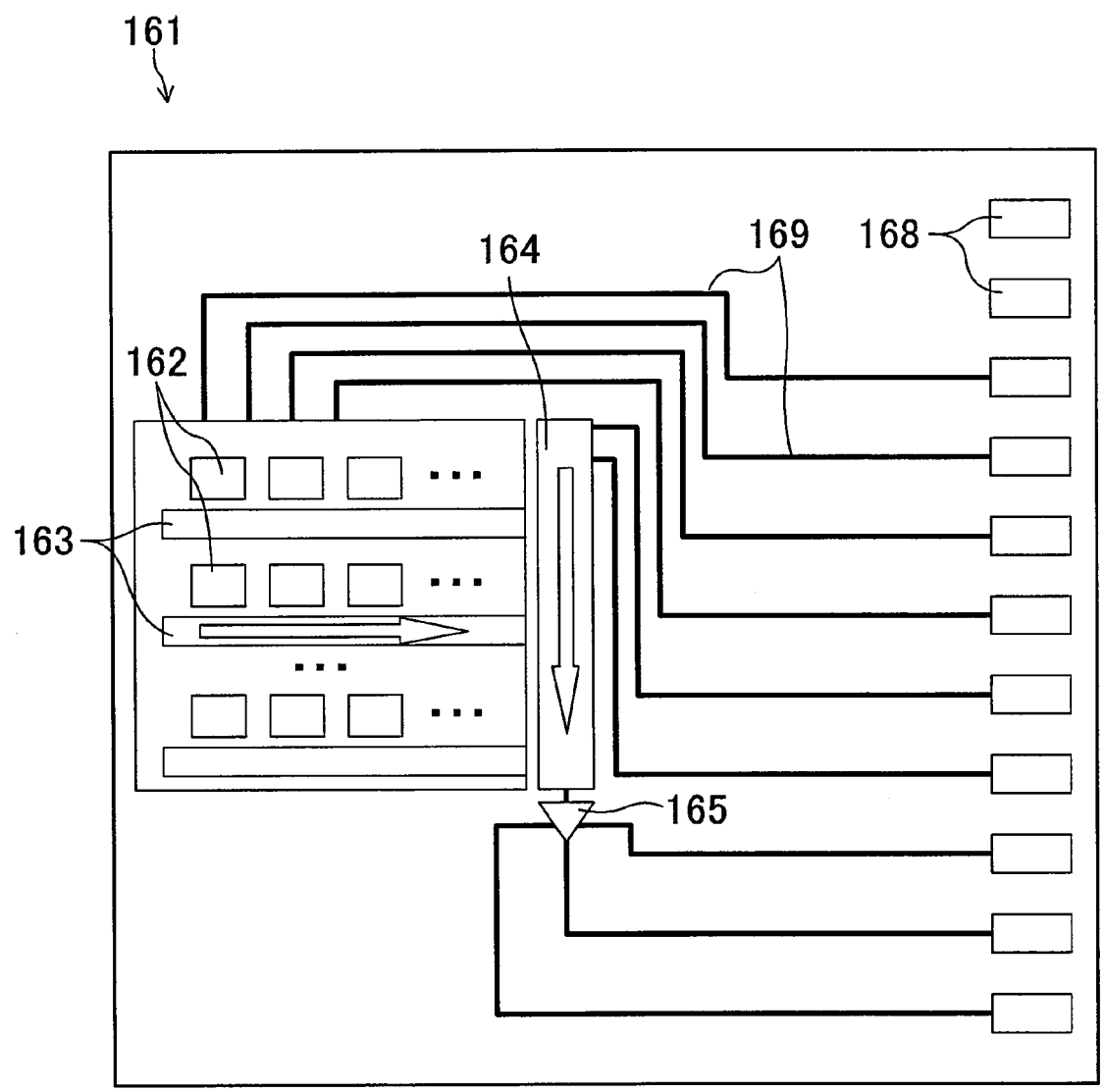
FIG. 10 is a plan view illustrating a solid-state imaging device in a conventional endoscope.

FIGS. 8A and 8B are a side view and a plan view, respectively, schematically illustrating imaging apparatus according to a sixth embodiment of the present invention. FIGS. 8A and 8B show an inner structure when viewed through a filler 48 and a tape automated bonding (TAB) substrate 51. The imaging apparatus of this embodiment has a shape whose length in the axial direction or longitudinal direction is larger than the lateral direction thereof, such as a tubular shape. Hereinafter, an endoscope will be described as an example of the imaging apparatus of this embodiment.

The endoscope of this embodiment includes: a lens (a camera lens: first optical member) 41 for focusing light; a prism (a second optical member) 42 for bending, to a right angle, the optical axis of incident light 49 which has passed through the lens 41; a solid-state imaging device 43 including an imaging region 44 and bonding pads 45; a board 46 having an upper face on which the solid-state imaging device 43 is fixed; a TAB substrate 51 connected to the bonding pads 45; bumps 47 serving as connecting members connecting the bonding pads 45 to the TAB substrate 51; and a filler 48 encapsulating the prism 42 and the solid-state imaging device 43. The shape of this endoscope is tubular. A power supply voltage is supplied to, for example, the solid-state imaging device 43 via a cable having a length of about several meters.

The prism 42 may bend the optical axis of incident light 49 to an angle except for a right angle and may be replaced with an optical member which changes the direction of light. An electronic substrate other than the TAB substrate 51 may be used. The bumps are made of a metal such as solder.

One of the solid-state imaging devices of the first through fifth embodiments is used as the solid-state imaging device 43. FIGS. 8A and 8B show an example employing the solid-state imaging device of the first embodiment which includes vertical CCDs (not shown) for transferring, in a first direction, signals subjected to photoelectric conversion at light-receiving parts and horizontal CCDs for transferring, in a second direction 60, the signals transferred through the vertical CCDs and in which the bonding pads 45 are arranged in two rows at a side of the imaging region 44 in the first direction.

The endoscope of this embodiment is provided with the solid-state imaging device whose width in the second direction is smaller than those of conventional devices. In addition, in the solid-state imaging device 43, the optical axis of incident light 49 entering the prism 42 through the lens 41 coincides with (i.e., is parallel to) the first direction. Accordingly, the outside diameter of the endoscope is smaller than those of conventional endoscopes. This enables the burden on patients to be greatly lessened in examination and endoscopic surgery. For industrial purpose, inspection of slender piping and internal inspection of machinery, which are impossible with conventional endoscopes, are also enabled.

Further, in the endoscope of this embodiment, the bonding pads 45 of the solid-state imaging device 43 are connected to the TAB substrate 51 via the bumps 47. Thus, even when the bonding pads 45 are arranged in a plurality of rows, the connecting members are not in contact with each other in connecting the bonding pads 45 to the TAB substrate 51. Wires may be, of course, used as connecting members. However, bumps are preferably used especially when the bonding pads 45 are arranged in a large number of rows or when the bonding pads 45 are not staggered but are arranged such that a first bonding pad row and a second bonding pad completely overlap each other when viewed in the first direction. That is, the use of bumps as connecting members greatly enhances the flexibility in arrangement of the bonding pads 45. The use of bumps as connecting members also further uniforms electrical resistances in these connecting members, as compared to the case of using wires, and greatly reduces variations in electrical resistance at the bonding pads 45.

In addition to the solid-state imaging device, a light source such as a light emitting device (an LED) may be incorporated in an insertion portion of the endoscope of this embodiment.

The endoscope is not necessarily tubular and a capsule endoscope may be used. In such a case, the use of the solid-state imaging devices of the first through fifth embodiments reduces the outside diameter of the endoscope.

As described above, a solid-state imaging device according to the present invention is useful for imaging apparatus, such as an endoscope, whose longitudinal length is larger than the lateral length thereof.

What is claimed is:

1. A solid-state imaging device, comprising:
an imaging region including a plurality of light-receiving parts for converting incident light into signals;
a first transfer section provided on the imaging region and transferring, in a first direction, the signals generated by the light-receiving parts;
a second transfer section provided at a first side of the imaging region in the first direction and transferring, in a second direction intersecting the first direction, the signals transferred from the first transfer section;
an output circuit for outputting the signals transferred from the second transfer section; and
a plurality of bonding pads provided at the first side of the imaging region with the second transfer section sandwiched between the imaging region and the bonding pads,
wherein the bonding pads are arranged in a plurality of rows each extending in the second direction, and
each of the bonding pads in one of the rows at least partially overlaps one of the bonding pads in another one of the rows when viewed in the first direction.

2. The solid-state imaging device of claim 1, wherein none of the bonding pads in one of the rows overlaps any of the bonding pads in another one of the rows when viewed in the second direction.

3. The solid-state imaging device of claim 1, further comprising lines each extending from one of the bonding pads to one of the imaging region, the second transfer section, and the output circuit, and
connection portions of some of the bonding pads connected to associated ones of the lines shift, in the second direction, from connection portions of the other bonding pads connected to associated ones of the lines depending on the locations of the bonding pads.

4. The solid-state imaging device of claim 1, further comprising bonding pads provided at a second side of the imaging region in the first direction,
wherein the bonding pads at the second side of the imaging region are arranged in a plurality of separate rows each extending in the second direction, and
each of the bonding pads in one of the rows at the second side of the imaging region at least partially overlaps one of the bonding pads in another one of the rows at the second side of the imaging region when viewed in the first direction.

5. The solid-state imaging device of claim 1, wherein each of the bonding pads at the first side of the imaging region is in the shape of a rectangle whose length in the first direction is larger than the length thereof in the second direction.

6. The solid-state imaging device of claim 1, further comprising a peripheral circuit provided at the first side of the imaging device with at least one of the bonding pads sandwiched between the peripheral circuit and the imaging region.

7. The solid-state imaging device of claim 1, wherein the first transfer section is vertical CCDs, and
the second transfer section is horizontal CCDs.

8. The solid-state imaging device of claim 7, wherein the bonding pads include an output pad for outputting the signals from the output circuit to outside the device, a power-supply pad, a ground pad, a substrate contact pad, a first drive pad for receiving a drive signal for the vertical CCDs, and a second drive pad for receiving a drive signal for the horizontal CCDs, and
the output pad is adjacent to one of the power-supply pad, the ground pad, and the substrate contact pad.

9. The solid-state imaging device of claim 1, wherein the first transfer section is vertical signal lines,
a second transfer section is a horizontal signal line, and
the signals generated by the light-receiving parts are read out to the vertical signal lines via MOS transistors.

* * * * *